(12) United States Patent
Rothenberg

(10) Patent No.: US 9,766,007 B2
(45) Date of Patent: Sep. 19, 2017

(54) COOLANT DEVICE, DISPENSER AND METHODS

(71) Applicant: Sarah Rothenberg, Jerusalem (IL)

(72) Inventor: Sarah Rothenberg, Jerusalem (IL)

( * ) Notice: Subject to any disclaimer, the term of this patent is extended or adjusted under 35 U.S.C. 154(b) by 410 days.

(21) Appl. No.: 14/367,867

(22) PCT Filed: Dec. 20, 2012

(86) PCT No.: PCT/IL2012/050539
§ 371 (c)(1),
(2) Date: Jun. 20, 2014

(87) PCT Pub. No.: WO2013/093917
PCT Pub. Date: Jun. 27, 2013

(65) Prior Publication Data
US 2015/0114858 A1   Apr. 30, 2015

Related U.S. Application Data

(60) Provisional application No. 61/578,962, filed on Dec. 22, 2011.

(51) Int. Cl.
*A61F 7/10* (2006.01)
*F25D 5/02* (2006.01)
(Continued)

(52) U.S. Cl.
CPC .............. *F25D 5/02* (2013.01); *A61F 7/106* (2013.01); *B65D 81/3266* (2013.01);
(Continued)

(58) Field of Classification Search
CPC ....................................................... F25D 2/05
(Continued)

(56) References Cited

U.S. PATENT DOCUMENTS 3,057,467 A    10/1962 Williams
3,255,872 A *   6/1966 Shaw ................. B65D 81/3272
                                                206/219
(Continued)

FOREIGN PATENT DOCUMENTS

CN         2304278Y  Y   1/1999
CN         1923168   A   3/2007
(Continued)

OTHER PUBLICATIONS

International Application Publication with Search Report of the International Searching Authority, Application No. PCT/IL2012/050539, date of mailing May 7, 2013, 4 pages, issued by USPTO, Alexandria, Virginia.

*Primary Examiner* — Avinash Savani
(74) *Attorney, Agent, or Firm* — Peter B. Scull; Hamilton, DeSanctis & Cha LLP

(57) ABSTRACT

This invention provides a thin and discreet coolant device, and single and multiple unit dispenser containers containing the same. The coolant device comprises a first packet being comprised of a waterproof or water-resistant material containing water therewithin and further comprising a fold and further adapted to have a selectively permanent connection between external and internal layers of said fold, such that upon applying a force to laterally extend the ends of said packet, a rupture of said first packet occurs allowing for the leakage of the water contained therewithin. The coolant device further comprises a second packet which encases said first packet, comprising an exterior and interior layer, wherein said interior layer is comprised of an absorbant material and said exterior layer is comprised of a waterproof or water-resistant material and wherein an amount of powdered urea is located within an interior of said second packet. Upon lateral extension of the sides of the second packet, a rupture of said first packet occurs allowing for the
(Continued)

leakage of the water contained therewithin and its exposure to said urea located within said second packet, which exposure results in an endothermic reaction resulting in an outer surface of said second packet becoming cooler to the touch than an outer surface temperature prior to said rupture. Use of the coolant devices to provide cooling to a skin surface on demand is described, as well.

6 Claims, 8 Drawing Sheets

(51) Int. Cl.
    B65D 81/32 (2006.01)
    A61F 7/00 (2006.01)
    A61F 7/02 (2006.01)
(52) U.S. Cl.
    CPC ........... A61F 2007/0052 (2013.01); A61F 2007/0269 (2013.01); A61F 2007/0271 (2013.01)
(58) Field of Classification Search
    USPC .................................... 126/263.07; 206/222
    See application file for complete search history.

(56) References Cited

U.S. PATENT DOCUMENTS

| | | | |
|---|---|---|---|
| 3,986,479 A | | 10/1976 | Bonk |
| 4,399,668 A | * | 8/1983 | Williamson ....... B65D 81/3883 215/12.1 |
| 4,780,117 A | * | 10/1988 | Lahey ................ A61F 7/106 126/263.07 |
| 4,856,651 A | * | 8/1989 | Francis, Jr. ............ A61F 7/03 126/263.07 |
| D328,792 S | * | 8/1992 | Salmon .................. D24/206 |
| 5,147,067 A | * | 9/1992 | Effertz ............ B65D 81/3879 220/739 |
| 5,702,375 A | | 12/1997 | Angelillo et al. |
| 5,956,963 A | | 9/1999 | Lerner |
| 6,770,064 B1 | | 8/2004 | Ruscher |
| 6,811,338 B1 | * | 11/2004 | Manske, Jr. .......... A01N 25/34 15/104.94 |
| 6,833,179 B2 | | 12/2004 | May et al. |
| 7,255,506 B2 | | 8/2007 | Gruenbacher et al. |
| 7,497,351 B2 | | 3/2009 | Amundson et al. |
| 7,565,987 B2 | * | 7/2009 | Bauer ................ B65D 75/30 206/438 |
| 7,588,548 B2 | | 9/2009 | Kopreski |
| 7,648,046 B2 | | 1/2010 | Sosalla et al. |
| 7,654,412 B2 | | 2/2010 | Amundson et al. |
| 7,884,037 B2 | | 2/2011 | Sirovatka et al. |
| 8,039,011 B2 | | 10/2011 | Flugge-Berendes et al. |
| 2002/0103520 A1 | * | 8/2002 | Latham .................. A61F 7/10 607/108 |
| 2003/0176904 A1 | | 9/2003 | Patterson |
| 2004/0193237 A1 | | 9/2004 | Krueger |
| 2005/0240251 A1 | | 10/2005 | Smith |
| 2007/0098769 A1 | | 5/2007 | Champion |
| 2007/0148448 A1 | | 6/2007 | Joseph et al. |
| 2007/0179465 A1 | * | 8/2007 | Sakakibara ............. A61F 13/84 604/385.01 |
| 2007/0198071 A1 | | 8/2007 | Ting et al. |
| 2007/0202184 A1 | | 8/2007 | Amundson et al. |
| 2007/0202185 A1 | | 8/2007 | Amundson et al. |
| 2007/0278242 A1 | | 12/2007 | Amundson et al. |
| 2007/0289988 A1 | | 12/2007 | Sosalla et al. |
| 2008/0087680 A1 | | 4/2008 | Amundson et al. |
| 2008/0145664 A1 | | 6/2008 | Sirovatka et al. |
| 2009/0065521 A1 | | 3/2009 | Amundson et al. |
| 2009/0124925 A1 | | 5/2009 | MacDonald et al. |
| 2009/0132013 A1 | | 5/2009 | Amalfi |
| 2009/0155325 A1 | | 6/2009 | Wenzel et al. |
| 2010/0159170 A1 | | 6/2010 | Wang et al. |
| 2010/0185267 A1 | | 7/2010 | Dickie |
| 2010/0204764 A1 | | 8/2010 | Garetz |

FOREIGN PATENT DOCUMENTS

| | | |
|---|---|---|
| EP | 0095814 A2 | 12/1983 |
| JP | S55152778 A | 11/1980 |
| JP | S59149976 A | 8/1984 |
| JP | H0298358 A | 4/1990 |
| JP | H02166375 A | 6/1990 |
| NO | 2007138498 A2 | 12/2007 |
| NO | 2007138498 A3 | 12/2007 |
| NO | 2008075230 A1 | 6/2008 |
| NO | 2009024837 A1 | 2/2009 |
| NO | 2009063340 A2 | 5/2009 |
| NO | 2009063340 A3 | 5/2009 |
| NO | 2009077896 A2 | 6/2009 |
| NO | 2009077896 A3 | 6/2009 |
| NO | 2010070470 A2 | 6/2010 |
| NO | 2011039661 A2 | 4/2011 |
| WO | 0187588 A2 | 11/2001 |
| WO | 03006536 A1 | 1/2003 |
| WO | 2004012575 A2 | 2/2004 |
| WO | 2005105105 A2 | 11/2005 |
| WO | 2007078362 A1 | 7/2007 |
| WO | 2009019644 A2 | 2/2009 |
| WO | 2009019644 A3 | 2/2009 |
| WO | 2010108132 A1 | 9/2010 |

* cited by examiner

Fig.1A
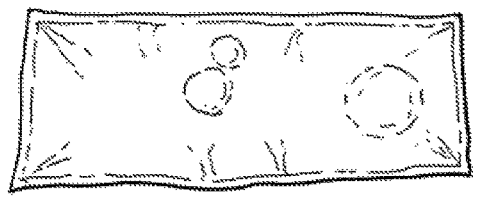
Fig.1B
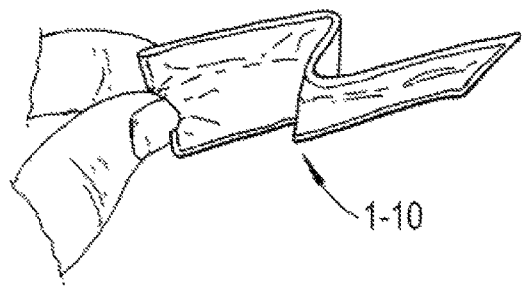
Fig.1C
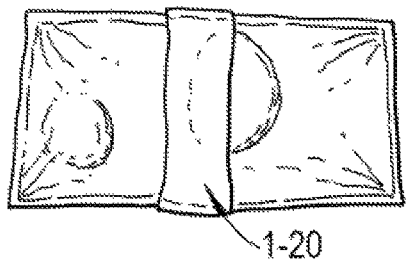
Fig.1D
Fig.1E
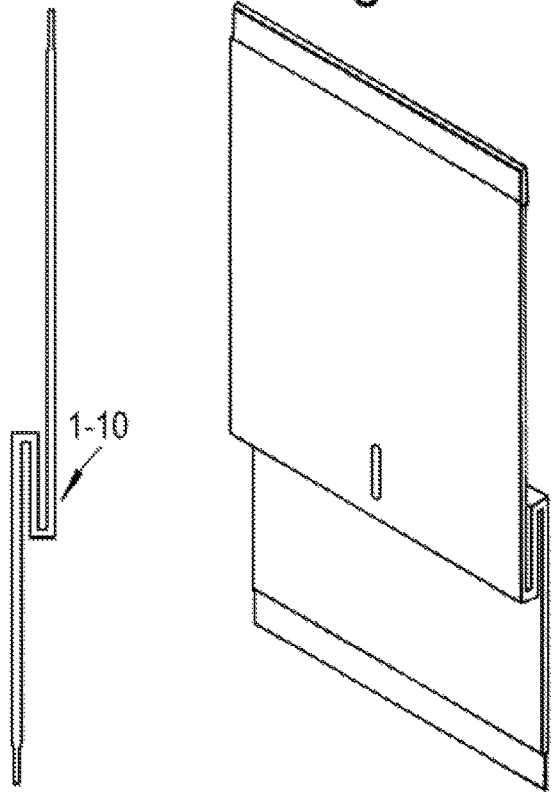

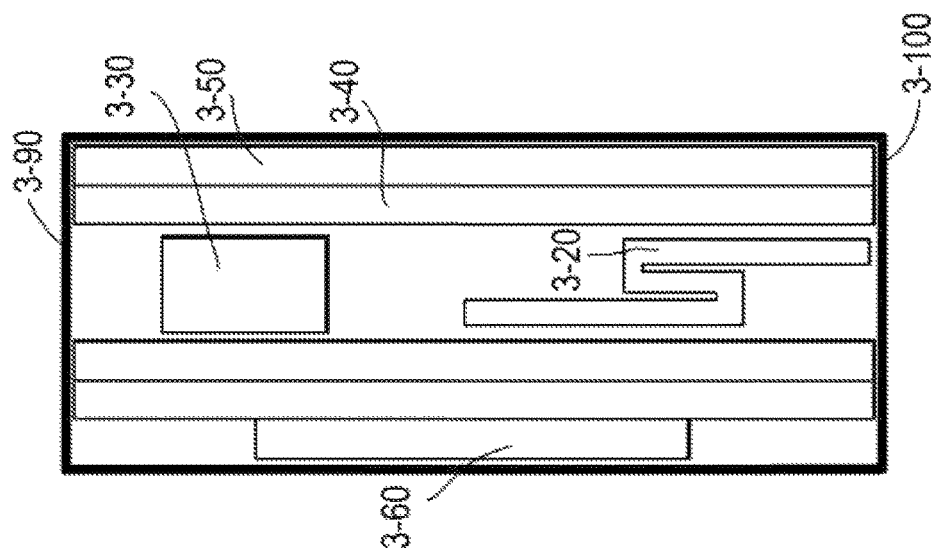
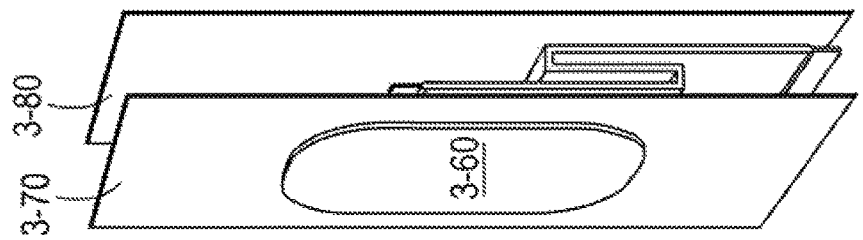
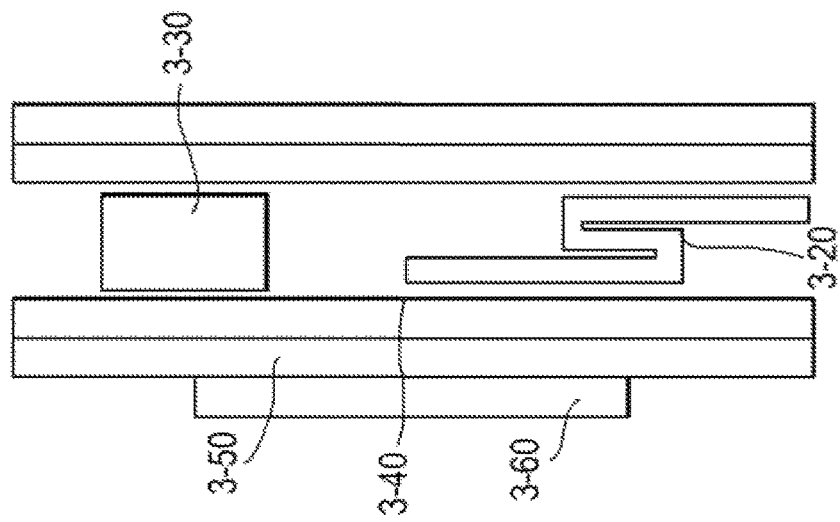

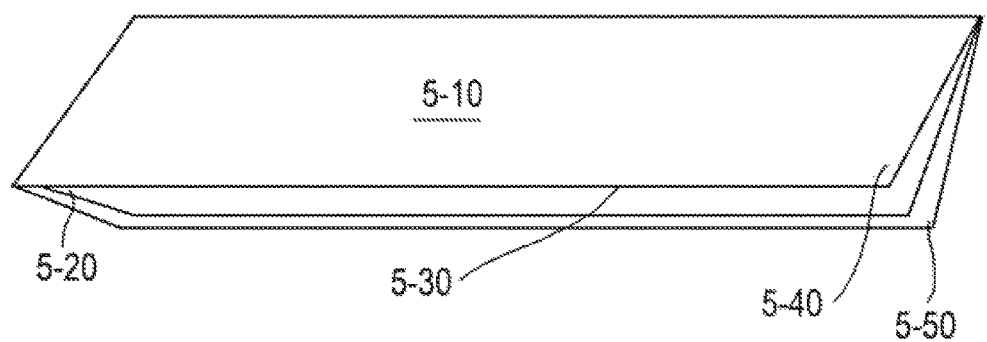
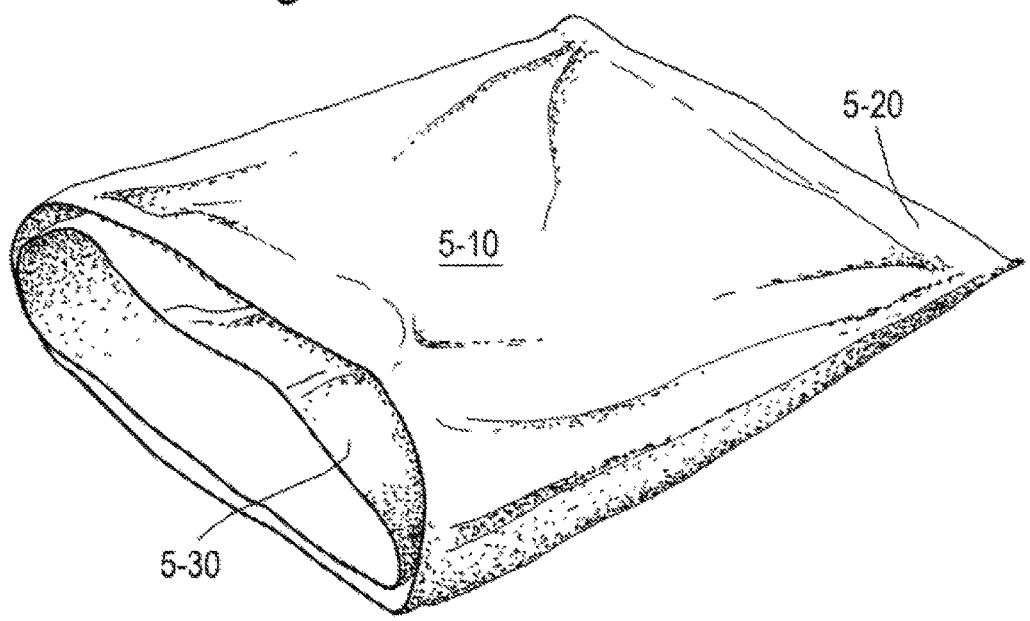

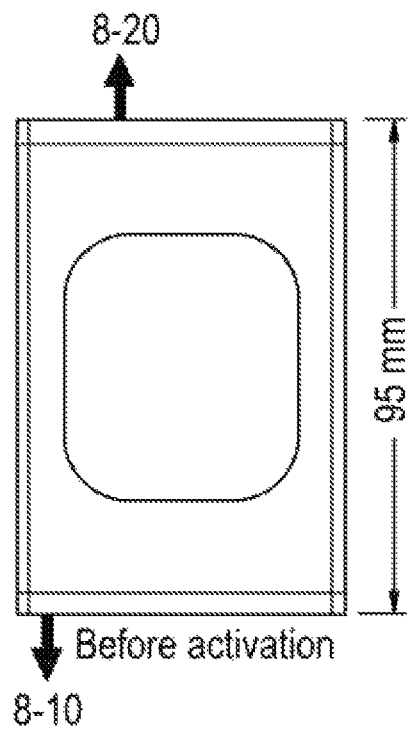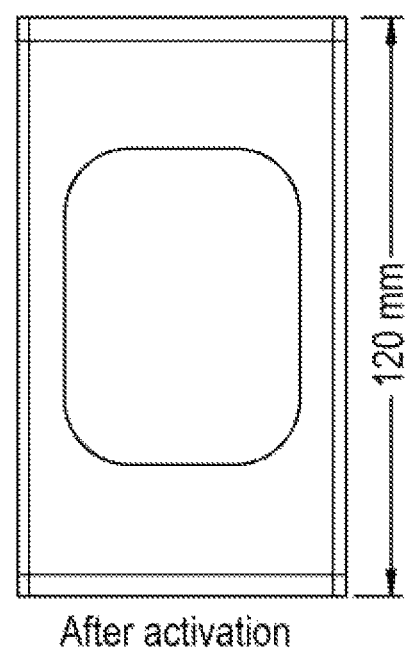

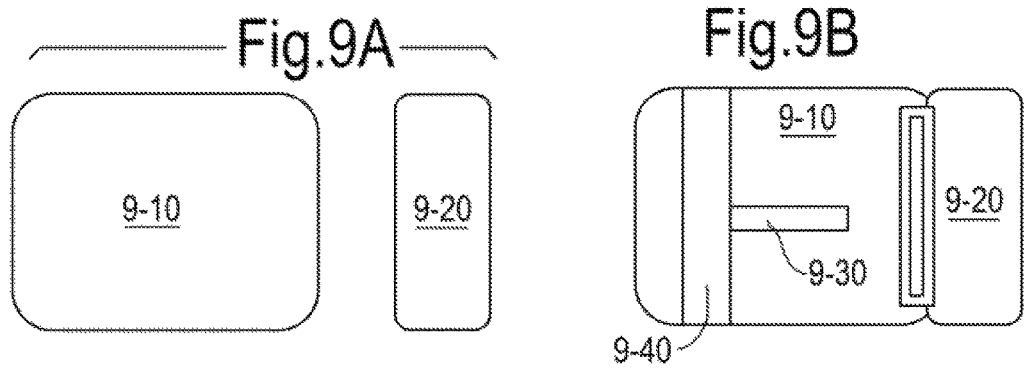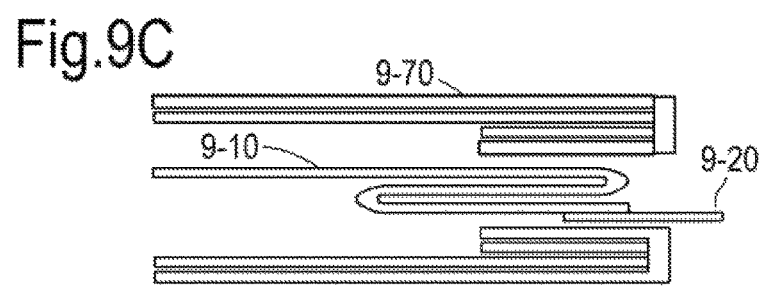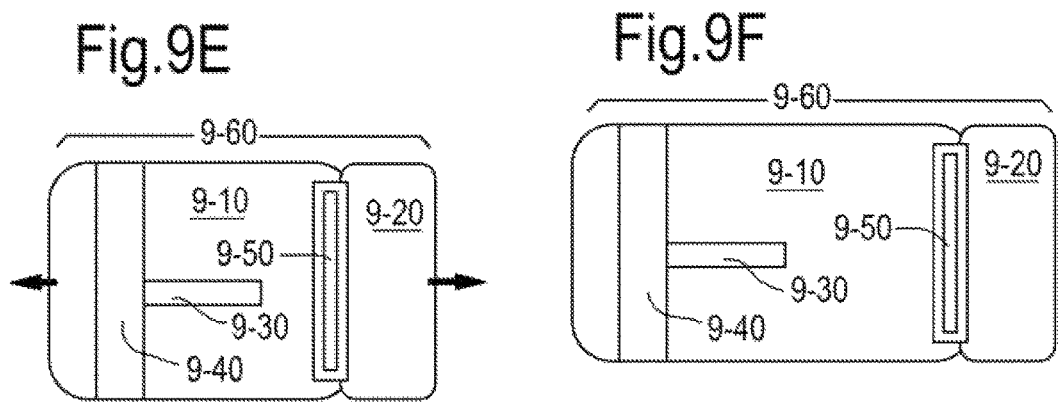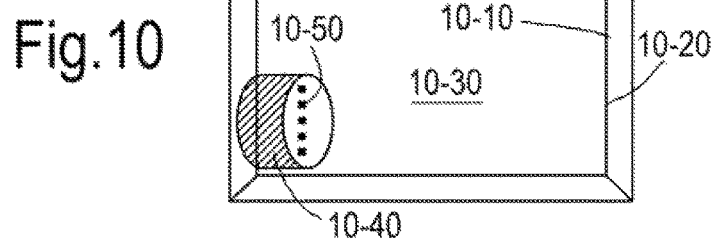

COOLANT DEVICE, DISPENSER AND METHODS

BACKGROUND OF THE INVENTION

This invention relates to a coolant device, dispenser apparatus and method for the application of the coolant device to appropriate skin surfaces of the human body to bring relief to the subject. More specifically, the invention relates to the application of cool or cold, discreet, thin tissue-like materials to the skin surface of a subject to alleviate symptoms and discomfort associated with heat, including in women experiencing hot flashes, individuals suffering from minor burns or fever, and other applications.

Hot flashes can occur at any time and at any place and are a source of considerable discomfort and consternation to many menopausal women. In the past, many women have resorted to using various forms of medication to lessen the effects of menopause and attendant hot flashes, yet these medications do not provide instant relief for the symptoms of hot flashes, nor do they mask the embarrassment of experiencing the same including experiencing a sudden onset in a public venue.

Women have found that applying cool or cold materials to the skin surface during the onset of a "hot flash" provides considerable and immediate relief to the discomfort of hot flashes.

Since hot flashes can occur at any time and at any place, including in very public venues, it therefore has been a challenge to find a socially acceptable means for reducing the awkward symptoms associated therewith.

While various types of cooling devices have been described previously for this purpose, such devices are quite bulky, and therefore do not provide effective cooling in a discrete manner.

There remains, therefore, a need for a means of alleviating the symptoms of hot flashes in a discreet and effective manner.

SUMMARY OF THE INVENTION

In some embodiments, the present invention provides a coolant device, and single and multiple unit dispenser containers containing the same.

In some embodiments, this invention provides a coolant device comprising a first packet, said first packet being comprised of a waterproof or water-resistant material and containing water sealed within said first packet, wherein said first packet comprises a fold, and said fold is further adapted to have a selectively permanent connection between external and internal layers of said fold, such that upon applying a force to laterally extend at least one end of said packet, a rupture of said first packet occurs allowing for the leakage of the water contained therewithin; and a second packet which encases said first packet, said second packet comprising an exterior and interior layer, wherein said interior layer is comprised of an absorbant material and said exterior layer is comprised of a waterproof or water-resistant material and wherein an amount of a compound whose solvation in water results in an endothermic reaction is located within an interior of said second packet; whereby upon lateral extension of at least one side of the second packet, a rupture of said first packet occurs allowing for the leakage of the water contained therewithin and its exposure to said compound located within said second packet, which exposure results in an endothermic reaction resulting in an outer surface of said second packet becoming cooler to the touch than an outer surface temperature prior to said rupture.

As used herein the term "urea" serves as a specific embodiment for any compound whose solvation in water results in an endothermic reaction, and reference to urea specifically should be understood to encompass such use of any other compound whose solvation in water results in an endothermic reaction, and any other embodiment of the same as referred to herein.

In some embodiments, this invention provides a coolant device comprising a first packet being comprised of a waterproof or water-resistant material containing water therewithin and further comprising a fold at, in one embodiment, substantially a midline of said packet, and in other embodiments, off-center of such midline, and in other embodiments, placed at any convenient point for such packet, further adapted to have a permanent connection between external and internal layers of said fold, such that upon applying a force to laterally extend the ends of said packet, a rupture of said first packet occurs allowing for the leakage of the water contained therewithin. The coolant device further comprises a second packet which encases said first packet, comprising an exterior and interior layer, wherein said interior layer is comprised of an absorbant material and said exterior layer is comprised of a waterproof or water-resistant material and wherein an amount of powdered urea is located within an interior of said second packet, which amount results in a ratio of the number of grams urea to the number of milliliters of water ranging from 5:1 to 0.5:1. In some embodiments, the amount of powdered urea is located within interior of said second packet, which amount results in a ratio of the number of grams urea to the number of milliliters of water ranging from 3:1 to 0.5:1. In some embodiments, the amount of powdered urea is located within of said second packet, which amount results in a ratio of the number of grams urea to the number of milliliters of water ranging from 1.5:1 to 0.5:1. The ratios can be adjusted to suit various sizes and permutations of the device, as will be appreciated by the skilled artisan and should be understood to be encompassed by this invention, as well.

Upon lateral extension of the sides of the second packet, a rupture of said first packet occurs allowing for the leakage of the water contained therewithin and its exposure to said urea located within said second packet, which exposure results in an endothermic reaction resulting in an outer surface of said second packet becoming cooler to the touch than an outer surface temperature prior to said rupture.

In some embodiments, the first packet is comprised of a low density polypropylene or a high density polypropylene, polyethylene, PVCD, nylon, and others as will be appreciated by the skilled artisan. In some embodiments, the first packet has dimensions of approximately between first packet has dimensions of approximately between 30-90 mm on a side. In some embodiments, these dimensions can be larger, as will be appreciated by the skilled artisan, when designing a thin packet for a desired purpose. In some embodiments, the dimensions can be larger or smaller, as will be appreciated by the skilled artisan.

In some embodiments, the second packet has dimensions of approximately between 35-70 mm wide. In some embodiments, the dimensions may be larger, from 35-250 mm wide. In some embodiments, the second packet has dimensions of approximately between 35-250 mm long. In some embodiments, the second packet has a thickness of between 5-25 mm. In some embodiments, the second packet has a thickness of between 5-10 mm, or in some embodiments, the second packet has a thickness of between 0.5-10 mm, or in some embodiments, the second packet has a thickness of between 0.5-5 mm. In some embodiments, the second packet has a thickness of less than 25 mm preferably less than 5 mm most preferably less than 3 mm. In preferred embodiments, the thickness may be 0.5-10 mm preferably 0.5-5 mm. In some embodiments, these dimensions can be varied to suit particular applications, and it is understood by the skilled artisan that the goal of providing a effective coolant device, for example, one discreet for use in settings requiring privacy, can be realized with different dimensions as well.

In some embodiments, the interior layer of said second packet is comprised of a non-woven material, and in some embodiments, such non-woven material may be a layer attached to said interior layer. In some embodiments, such non-woven material may comprise polypropylene or polyethylene. The attachment of the non-woven fabric to the interior layer of said second packet may be by welding at the edges of both layers. The size of the non-woven fabric may be the same size as the second packet, or in some embodiments, the size is less than that of the second packet. In some embodiments, the interior layer of said second packet is comprised of an absorbent material, such as that described in U.S. Pat. Nos. 4,381,783, 5,944,706 or 5,411,497.

In some embodiments, the exterior layer of said second packet is comprised of a low density polypropylene or a high density polypropylene.

In some embodiments, the second packet is comprised of composite materials such as film-coated nonwoven webs, and micro-porous films such as manufactured by Mitsui Toatsu Co., of Japan under the designation ESPOIR NO and by EXXON Chemical Co., of Bay City, Tex., under the designation EXXAIRE, or in some embodiments, such materials are comprised of polymer blends for example, as available from Clopay Corporation, Cincinnati, Ohio under the name HYTREL blend P18-3097, or in some embodiments, materials as described in PCT Application No. WO 95/16746, or U.S. Pat. No. 5,571,096.

In some embodiments, the exterior surface of said second packet is further modified to incorporate a region containing a thin, soft, absorbent material, for example, absorbant to any secretions on a skin surface to which the packet/device is applied, to provide added comfort to the user. In some embodiments, such thin absorbent material may improve the feel of the material, imparting a feel that is soft to the touch. According to this aspect and in some embodiments, the region comprises strips or small pieces of said thin, absorbent material placed at multiple regions on said exterior surface of said second packet.

In one embodiment, the present invention provides a single unit dispenser container containing a coolant device as herein described. In some embodiments, at least one lateral surface of said second packet is fixedly adhered to an internal surface of said dispenser, such that, in order to extricate said second packet from said dispenser, at least a moderate force must be applied thereto, such moderate force being sufficient to cause a rupture in said first packet, releasing water located within said first packet into an interior of said second packet. In some embodiments, at least two lateral surfaces of said second packet are selectively fixedly adhered to an internal surface of said dispenser; and said dispenser contains a perforation along its upper or lower outer surface such that, applying pressure to an outer upper or lower surface, which does not contain said perforation results in a rupture in said first packet, releasing water located within said first packet into an interior of said second packet; and partial expulsion of said second packet from said dispenser.

In some embodiments, at least one lateral surface of said second packet fixedly adhered to an internal surface of said dispenser is seamed within an edge of said dispenser. In some embodiments, at least one lateral surface of said second packet comprises at least one perforation at a region proximal to an area of seaming of said lateral surface.

This invention also provides a multiple unit dispenser container comprising the coolant device as herein described. In some embodiments, the dispenser container is in the form of a box of packets, comprising at least one top surface which is substantially rigid, and wherein said top surface comprises a slit like opening, which opening has a depth sufficient to accommodate minimal engagement of a lateral surface of said second packet therewithin; and said slit like opening is of a width that is narrower than a width at the region of said fold in said first packet, such that, upon extrication of said second packet from said dispenser, at least a moderate force must be applied thereto, such moderate force being sufficient to cause a rupture in said first packet, releasing water located within said first packet into an interior of said second packet.

In some embodiments, the container comprises a series of coolant devices which are attached to each other end to end within said dispenser. In some embodiments, the series of coolant devices which are attached to each other end to end within said dispenser comprise perforations at a region of attachment between said coolant devices.

In some embodiments, this invention provides a method for combating discomfort associated with a rise in temperature at a skin surface, said method comprising:

laterally extending at least two sides of a second packet of a coolant device as herein described to cause a rupture of said first packet allowing for the leakage of the water contained therewithin and its exposure to said urea located within said second packet, which exposure results in an endothermic reaction resulting in an outer surface of said second packet becoming cooler to the touch than an outer surface temperature prior to said rupture resulting in an activated coolant device; and applying said activated coolant device to a skin surface for which the application of the same results in an alleviation of said discomfort on demand.

In some embodiments, the said coolant device is extricated from the single unit dispenser as herein described, and in some embodiments, the coolant device is extricated from the multiple unit dispenser container as herein described.

In some embodiments, this invention provides a coolant device, comprising:

a first packet, said first packet being comprised of a waterproof or water-resistant material and containing an amount of a compound whose solvation in water results in an endothermic reaction therewithin;

a second sealed packet comprising an inner layer comprised of a waterproof material which encases said first packet, said second packet comprising water and said first packet sealed therewithin, wherein selective rupture of said first packet within said second packet promotes leakage of said compound from said first packet and mixture of said compound with said water;

whereby said leakage results in the occurrence of an endothermic reaction within said second sealed packet resulting in an outer surface of said second packet becoming cooler to the touch than an outer surface temperature prior to said rupture.

In some embodiments, a rigid material is incorporated within the packaging such that selective pressure to the rigid material preferentially perforates or punctures the first packet. In some embodiments, the waterproof or water-resistant material of the first packet is a thin envelope or wrapping material, which material is perforated at a region, whereby such perforation makes rupture of the packet at such region more readily accomplished, however, leakage of the compound contained therewithin until the intended rupture of such packet.

In some embodiments, the first packet comprises a dispersing agent which facilitates dispersion of the compound within the water following said rupture. In some embodiments, the first packet is comprised of a material that is substantially hydrophobic. According to this aspect, and in some embodiments, the first packet is comprised of a material or contains a material therewithin that promotes rapid access and distribution of the compound within the water, following rupture of the first packet.

In some embodiments, any embodiment as described herein with regard to the first and/or second packets and/or kits comprising the same and/or uses thereof are applicable for any embodied coolant device as herein described.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or sub-range within the stated ranges, optionally including or excluding either or both endpoints, in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

BRIEF DESCRIPTION OF THE DRAWINGS

FIG. 1 is a photograph of an embodied first packet of an embodied cooling device of this invention. Spot welding of a midline fold is evident, which should be understood to be positionable at any desired region, as described.

FIG. 3 schematically depicts the various elements of an embodied cooling device of this invention and their arrangement within a single unit dispenser.

FIG. 5 schematically depicts another embodiment of a single use dispenser of the invention and a principle of operation thereof.

FIG. 8 schematically depicts another embodiment of a basic activation mechanism for an embodied cooling device of this invention and dimensional changes in this embodiment, following activation of the mechanism.

FIG. 9 depicts yet another embodiment of the assembly and organization of an embodied cooling device of this invention, including potential welding lines for such assembly.

FIG. 10 depicts another embodiment of an embodied cooling device of this invention.

DETAILED DESCRIPTION OF THE PRESENT INVENTION

Figure 2A:
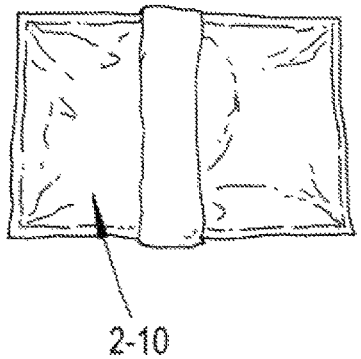
FIG. 2 is a photograph of an embodied first packet, second packet and single unit dispensers of an embodied cooling device of this invention.
Figure 2B:
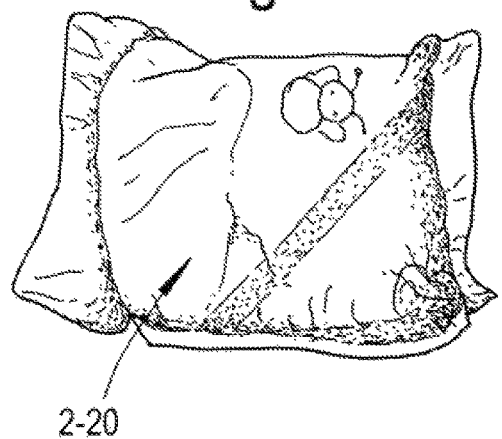
Figure 2C:
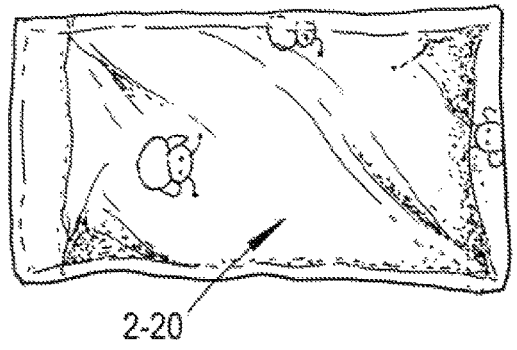

This invention provides, inter alia, a coolant device, and single and multiple unit dispenser containers containing the same.

The present inventions are directed toward devices that can discreetly provide in a tissue-like material, a device which undergoes an endothermic reaction on demand, whose application to a skin surface provides for a rapid cooling effect when applied thereto.

Such devices are suited, inter alia, for the alleviation of discomfort associated with a number of conditions, including hot flashes, as a result of menopause or other endocrine disorders, light to mild burns, heat due to elevated temperatures, fever, inflammation and others, as will be appreciated by the skilled artisan.

Hot flashes are associated with hormonal changes in menopausal women. The hormonal imbalances generate excess heat that the body must disperse. The symptoms of hot flashes include a precipitous and extreme sensation of heat, which can be accompanied by the production of sweat, including copious amounts of sweat. Such symptoms may result in a sudden and obvious flushing of the skin of the face and rapid production of sweat from facial glands, that is readily noticeable.

In some embodiments, the cooling devices of this invention are specifically designed to be discreet. In some embodiments, as the potential for embarrassment is high for the female subject, she may discreetly extricate the cooling tissue as herein described, from an ordinary dispenser, or in some embodiments, from a dispenser specifically designed to facilitate activation of the cooling mechanism, as herein described, to provide a rapid cooling to the affected regions, and thereby mitigate her discomfort and embarrassment.

Toward this end, in addition to the outermost or exposed packet being comprised of an exterior layer which is waterproof or water-resistant material, such layer may be aesthetically pleasing, and may be of an appropriate color, such as white, or light yellow or pink, so that the package assumes an appearance quite similar to a tissue, which may serve, in some embodiments, as a means for maintaining the use of the same as discreet.

While one application of the cooling devices of this invention is to be specifically discreet, such aspect is not a requirement and indeed one could envision uses of the device whereby such use may be readily apparent to the public.

In some embodiments, when it is desirable to make use of a cooling device, which is aesthetically pleasing and eye-catching, for example, and representing one embodiment, whereby, in pediatric applications, in order to increase compliance with a younger subject, the cooling device may specifically incorporate designs that appeal to children.

For example, and in one embodiment, childhood experiences in the summer often result in mild sunburn, which condition could be readily helped with the use of the cooling devices of this invention.

According to this aspect, and in some embodiments, as will be appreciated by the skilled artisan, one could readily envision specific deposition of a powdered compound whose solvation in water results in an endothermic reaction at discreet sites within the second packet and incorporating a thermochromic dye or coloring agent on an outer surface of said second packet, or visible through an outer surface of said second packet, which specifically changes color upon contact of the compound with water (and resulting chemical change), so that when the cooling device is activated and the endothermic reaction commences, a discernable pattern is created in the outer packet that is observable by eye.

Examples of thermochromic dyes are well known, for example as described in U.S. Pat. No. 4,028,118; U.S. Pat. No. 4,421,560; U.S. Pat. No. 5,858,914; U.S. Pat. No. 6,196,241; U.S. Pat. No. 6,196,241 and others. Such dyes may be specifically applied, or example via printing to desired regions of the coolant device, so that when activated, a desired pattern may emerge.

Such pattern may assume pleasing shapes, or other aesthetic designs, for example, cars, dogs, etc., or familiar cartoon characters. It will also be understood, that a pattern which may change color depending upon the temperature range present may be included in the coolant device. For example, certain hues may be emphasized when the temperature has dropped, which hues may intensify or change, as greater cooling is achieved, with the return to the first color profile as the coolant effect wears off.

The emergence of such patterns upon activation may serve as a means of increasing compliance of use, which may be particularly helpful, for example, when treating children.

In some embodiments, in accordance with this aspect, the exterior layer of the second packet may be of a transparent material, and the thermochromic agent may be printed on the outer surface of the interior layer of the second packet such that the transparent exterior layer prevents skin contact with the thermochromic agent, yet provides for clear visibility of the emerging pattern or design.

The key to the effectiveness of the cooling devices of this invention is the cooling mechanism. For example, when a subject begins to experience a "hot flash", or other source of discomfort due to elevated body temperature or heat at a particular region of the body, he/she can remove the cooling tissue from the dispenser in a manner which activates the cooling tissue, and/or manually activate the cooling tissue and within a very short period of time, begin to experience a soothing cooling sensation. The relief can be almost immediate, thereby rendering it superior to other products which often take a significant amount of time to be effective and do not provide for the unique advantages of the cooling tissues as herein described.

Another advantage to the cooling devices of this invention is the provision of a disposable device, which provides rapid cooling.

Another advantage to the cooling devices of this invention is the provision of a cooling device in a discreet package, which provides rapid cooling, with a reasonably long duration.

Another advantage to the cooling devices of this invention is the provision of a cooling device, which is aesthetically pleasing, and may serve as a novelty item, which in turn may encourage greater compliance in use in children.

Another advantage to the cooling devices of this invention is the provision of a cooling device, which may serve as a societal unifying emblem, which is relatively inexpensive. For example, one could readily envision a device whereupon a National emblem or flag has been printed, where fans, for example, watching an independence day celebration or parade may readily benefit from the cooling advantage, thereby prolonging their participation in the event, and extending national pride, given the number of people at the event that may each use the device, which would be at a cost within most citizens' grasp.

In some embodiments, the inventions is a coolant device, comprising a first packet, the first packet being comprised of a waterproof material and containing water; a second packet comprising a waterproof material which encases the first packet, said second packet containing in its interior an amount of a compound whose solvation in water results in an endothermic reaction therewithin and the first packet sealed therewithin, wherein rupture, preferably selective rupture, of the first packet within the second packet promotes leakage of water from the first packet and mixture of water and compound; wherein the coolant device has a thickness of about 0.5-10 mm, preferably 0.5-5 mm. In some embodiments the leakage results in the occurrence of an endothermic reaction within the second packet resulting in an outer surface of the second packet becoming cooler to the touch than an outer surface temperature prior to said rupture.

In some embodiments, this invention provides a coolant device comprising a first packet being comprised of a waterproof or water-resistant material containing water therewithin.

In some embodiments, the first packet is comprised of a low density polypropylene or a high density polypropylene.

In some embodiments, the first packet has length and height dimensions of approximately between 30 and 220 mm (each side).

The first packet may further comprise a fold further adapted to have a selectively permanent connection between external and internal layers of said fold, such that upon applying a force to laterally extend the ends of said packet, a rupture of said first packet occurs allowing for the leakage of the water contained therewithin.

In other embodiments, the first packet may further comprise a tab or appendage having a strong selectively permanent connection between it and an external surface of said fold, such that upon applying a force to the tab or appendage applies lateral pressure to a region of said packet, causing a rupture of said first packet, allowing for the leakage of the water contained therewithin.

In some embodiments, the term "selectively permanent" is to be understood to refer to the existence of a reasonably strong connection between indicated parts, for example, according to this aspect, between the external and internal layers of the fold of the first packet containing the water, such that rupture of the first packet by chance occurrence is prevented, for example during storage or transport of the device of this invention. The term "selectively permanent" is to be understood therefore, to refer to a specific and intended ability to rupture the indicated parts, for example, and according to this aspect, rupture of the first packet by selectively applying pressure to at least one lateral portion of the second packet, to promote rupture of the first packet, and thereby activate the endothermic reaction as herein described.

In some embodiments, according to this aspect, the fold of the first packet is at substantially a midline of the first packet. In some embodiments, such a fold is located more proximally to a terminus of the packet.

The coolant device according to this aspect, further comprises a second packet which encases said first packet, wherein said second packet comprises an exterior and interior layer, and wherein said interior layer is comprised of an absorbant material and said exterior layer is comprised of a waterproof or water-resistant material In some embodiments according to this aspect, the first packet has length and height dimensions of approximately between 30-90 mm each side. In some embodiments, the second packet has length and height dimensions of approximately between 35-250 mm wide and between 35-250 mm long. In some embodiments the device has a thickness of between 0.5-25 mm, or in some embodiments, between 3-25 mm. In some embodiments the device has a thickness of less than 10 mm, for example, preferably less than 5 mm, or less than 3 mm or in some embodiments, from 0.5 to 5 mm.

In some embodiments, as referred to throughout the application, the first packet is seamed with the second packet, at least partially, or completely. In some embodiments, as referred to throughout the application, the second packet constitutes an independent encasing package and the first packet is placed therein but is not seamed within the second packet.

In some embodiments, according to this aspect, the interior layer of said second packet is comprised of non-woven fabric (e.g. comprising polyethylene or polypropylene fibers), or any material which can be assembled to form a very thin layer of absorbant material. In some embodiments, use of the non-woven material further provides for an even distribution/surface for the endothermic reaction to promote even cooling efficacy throughout the device. In some embodiments the non-woven material is a non-woven fabric, and in some embodiments, the non-woven material or fabric is welded to a layer of the second packet comprising the waterproof material thereby forming an inner layer of the second packet. In some embodiments, it is laminated and in some embodiments, it is bi-layered. In some embodiments, reference to a non-woven fabric is applicable to any appropriate non-woven material for the purpose of this invention. In some embodiments the non woven fabric of the interior layer of the second packet is the same size as the outer layer of the second packet. In some embodiments, the material further provides a sensation similar to that of touching a tissue, which may be an added comfort factor for the user.

In some embodiments, according to this aspect, the exterior layer of said second packet is comprised of a low density polypropylene or a high density polypropylene, polyethylene or any appropriate material with a film.

The second packet according to this aspect, further comprises an amount of a compound whose solvation in water results in an endothermic reaction located within an interior of said second packet, Upon lateral extension of the sides of the second packet, a rupture of said first packet occurs allowing for the leakage of the water contained therewithin and its exposure to said urea located within said second packet, which exposure results in an endothermic reaction resulting in an outer surface of said second packet becoming cooler to the touch than an outer surface temperature prior to said rupture.

In some embodiments, the compound whose solvation in water results in an endothermic reaction is present in powdered form.

Figure 2D:
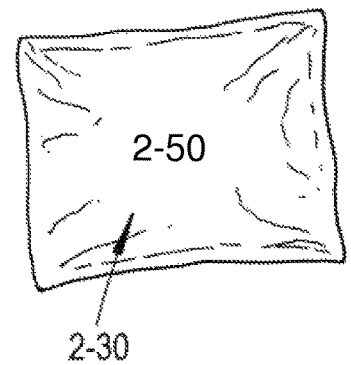
Figure 2E:
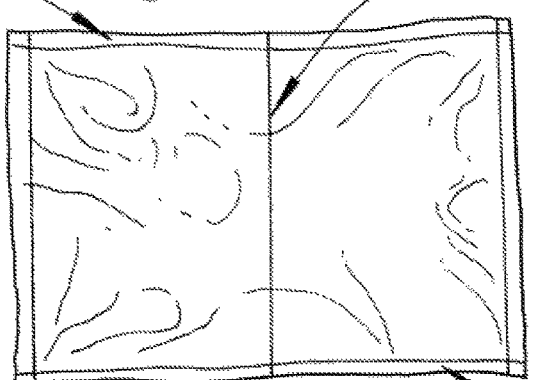

Referring to FIG. 1, an embodiment of a cooling device component is shown. According to this aspect, the first packet 1-10 is shown, containing water located therewithin and containing a welded region 1-20, which when pulled would cause rupture of the bag. FIGS. 1A-1C provide a diagram of an embodied packet, and FIGS. 1D-1E pictorially depict the packet, presented in a side and front view. In FIG. 2, the component of FIG. 1 is shown, as is its placement within a second packet containing a compound whose solvation in water results in an endothermic reaction dispersed therewithin. The first packet 2-10 is shown in FIG. 2A, which is inserted within the second packet, 2-20, shown in FIG. 2B. Comparing FIGS. 2B and 2C demonstrates the activation of the cooling mechanism, which can in turn, result in an elongation of the coolant device. The non-activated assembled coolant device 2-30 can be inserted in a packaging container 2-50 (FIGS. 2D and 2E). A potential welding scheme is shown in FIG. 2E, with potential welding lines highlighted 2-40.

FIG. 3 is discussed in detail in Example 3 below, and provides a cut-away view of the assembly of parts of an embodied cooling device of this invention, including a depiction of the first packet 3-20, and its positioning within the second packet comprised of an outer and inner layer seamed together, with urea in this aspect being dispersed within the void of the second packet.

FIG. 4 depicts in FIGS. 4A-4G an embodied assembly of an embodied cooling device of this invention. Welding lines 4-20, 4-30 and 4-40 are described, creating the packets as described herein, and provide a means to create a seal in the packet in order, for example, to contain the water and other materials within the packet to prevent leakage from said packets. Folding 4-10 of the first packet is depicted, as well. FIGS. 4H-4J depict an embodied container for removal of individual cooling devices of this invention, which removal may also activate the cooling mechanism.

FIG. 5 presents another embodied placement of the wipe within a packaging material.

Figure 7A:
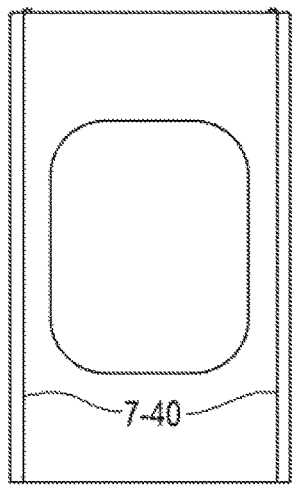
FIG. 7 schematically depicts another embodiment of the assembly and organization of an embodied cooling device of this invention, including potential welding lines for such assembly.
Figure 7B:
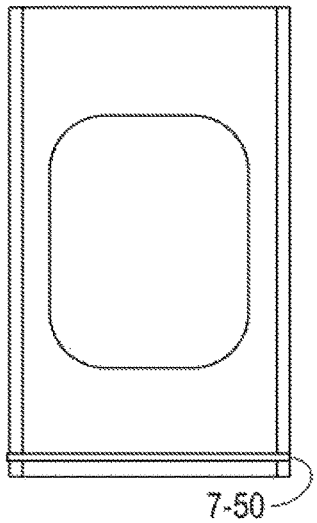
Figure 7C:
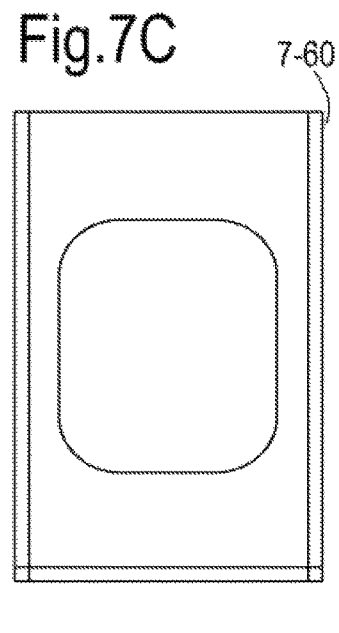

FIG. 6 presents a schematic arrangement of potential welding lines for the first packet, which when accomplished will result in rupture of the packet and release of the water contained therewithin. Further description of potential welding patterns is provided in FIG. 7. Once the first packet is placed within the second packet, and the second packet is seamed accordingly, it is evident that upon engagement of the cooling mechanism, a length of the second packet extends with the rupture and release of the welding of the first packet (compare FIG. 8A to FIG. 8B).

In another embodiment of the cooling device (FIG. 9), a tab 9-20 is attached to a region of the first packet 9-10, which tag is comprised of a material of an appropriate strength, such that pulling on the tab selectively releases the selectively permanent connection of the fold on the packet, thereby creating the rupture of the first packet and initiation of the cooling mechanism. The packet 9-60 contains a terminal modification such that the tab 9-20 extends outward therefrom. The first packet may contain welded regions, for example, 9-30 and 9-40 to weld top and bottom layers of the packet to each other, as desired. Positioning of the first packet 9-60 within the second packet 9-70 may be such so as to ensure that the tab of the first packet is accessible through the second packet (see FIG. 9C).

In another embodiment, this invention provides a coolant device, comprising:

a first packet, said first packet being comprised of a waterproof or water-resistant material and containing an amount of a compound whose solvation in water results in an endothermic reaction therewithin;

a second sealed packet comprising water and said first packet sealed therewithin, wherein selective rupture of said first packet within said second packet promotes leakage of said compound from said first packet and mixture of said compound with said water;

whereby said leakage results in the occurrence of an endothermic reaction within said second sealed packet resulting in an outer surface of said second packet becoming cooler to the touch than an outer surface temperature prior to said rupture.

FIG. 10 schematically depicts an embodiment of a coolant device of this invention in accordance with this aspect. In this embodied aspect, a first packet 10-40 is contained within a second packet 10-30. The outer surface of the second packet 10-20 may be further modified to comprise absorbent material for example in strips, as described for other embodied coolant devices of this invention. The absorbent strips may be soft to the touch. The inner surface 10-10 envelopes the first packet 10-40 contained therewithin. In some embodiments, the first packet comprises a dispersing agent which facilitates dispersion of said compound within said water following said rupture. In some embodiments, the first packet is comprised of a material that is substantially hydrophobic.

In some embodiments, the waterproof or water-resistant material of the first packet is a thin envelope or wrapping material, which material is perforated at a region 10-50, whereby such perforation makes rupture of the packet at such region more readily accomplished, however, prevents leakage of the compound contained therewithin until the intended rupture of such packet.

In some embodiments, the compound whose solvation in water results in an endothermic reaction is present in a ratio of the number of grams of said compound to the number of milliliters of water ranging from 3:1 to 0.5:1. In some embodiments, the compound whose solvation in water results in an endothermic reaction is present in a ratio of the number of grams of said compound to the number of milliliters of water ranging from 10:1 to 3:1, or in some embodiments, from 5:1 to 1:1, or in some embodiments, from 3:1 to 0.1:1, or in some embodiments, from 1:1 to 0.001 to 1.

In some embodiments, the compound whose solvation in water results in an endothermic reaction is urea, ammonium nitrate, ammonium chloride or potassium chloride.

In some embodiments, the exterior surface of said second packet is further modified to incorporate a region containing a soft, thin, absorbant material. In some embodiments, the region comprises strips or small pieces of thin, absorbent material placed at multiple non-contiguous regions on the exterior surface of the second packet.

In some embodiments, this invention can be considered to provide a unique, flexible coolant device which device finds broader applications, as it does not suffer the limitations of existing coolant packs. In some embodiments, the coolant device of this invention will comprise:

a first packet, being comprised of a waterproof or water-resistant material and containing water sealed within said first packet, wherein said first packet comprises a fold, and said fold is further adapted to have a selectively permanent connection between external and internal layers of said fold; and a second packet which encases said first packet, said second packet comprising an exterior and interior layer, wherein said exterior layer is comprised of a waterproof or water-resistant material and wherein an interior of said second packet comprises a reagent;

whereby contact of said reagent with water liberated from said first packet results in an endothermic reaction within said second packet.

In some embodiments, such a reagent according to this aspect may include urea, as described an exemplified herein, and the skilled artisan will appreciate that in a similar manner, reagents such as ammonium nitrate, ammonium chloride and potassium chloride may be used.

In some embodiments, this invention can be considered to broadly encompass any coolant device, which device is flexible, and has a thickness of between 5-25 mm, or in some embodiments, the device has a thickness of 0.5-10 mm, or in some embodiments, the device has a thickness of 0.5-5 mm and which comprises a discrete component containing water initially separated from the compound whose solvation in water results in an endothermic reaction, whereby a physical manipulation of the device results in the co-mixing of the water and compound stimulating the endothermic reaction and thereby providing rapid cooling in a discreet, thin device.

In some embodiments, the invention contemplates a single use dispenser, whereby the coolant device is activated upon removal from the single use dispenser. FIG. 5 schematically depicts an embodiment of a single use dispenser of the invention and a principle of operation thereof, in accordance with this aspect. The figure illustrates a cut-away view of the dispenser 5-10 containing the wipe, showing the coolant device 5-30 contained therewithin. At one end, the coolant device is seamed with the packaging 5-20, and may contain a slight seaming of the edge of the device therein, in some embodiments, or may contain a perforation at a region proximal to the seaming on the device. The other edge of the coolant device located proximally to the opening edge 5-50 is not seamed together with the dispenser package, such that ends 5-40 and 5-50 are seamed together, and a marking is placed on the outer side of the package indicating that the package should be torn at such end. When the package is torn, the coolant device is accessible and a tug on the same activates the cooling mechanism as described herein. FIG. 5B provides an example of a package thus torn.

While the described invention specifically exemplifies the use of urea and water as the elements within the coolant device for creating an endothermic reaction, it will be appreciated that other reagents may be used, for example, the urea may be replaced with ammonium nitrate, ammonium chloride, potassium chloride, etc., which in turn may also produce an endothermic reaction, or in some embodiments, the second packet of the coolant device may comprise a mixture of the same. The skilled artisan will appreciate that the ratios and amounts of water and such compound whose solvation in water results in an endothermic reaction may then be varied from that disclosed herein.

It will be apparent to those skilled in the art that various modifications and variations can be made in the cooling devices, dispensers and methods of the present invention without departing from the spirit or scope of the invention.

In some embodiments, the term "comprise" or grammatical forms thereof, refers to the inclusion of the indicated components of this invention, as well as inclusion of other active agents, and pharmaceutically acceptable carriers, excipients, emollients, stabilizers, etc., as are known in the pharmaceutical industry.

In one embodiment, the present invention provides combined preparations. In one embodiment, the term "a combined preparation" defines especially a "kit of parts" in the sense that the combination partners as defined above can be used independently or in different combinations i.e., simultaneously, concurrently, separately or sequentially.

EXAMPLES

Example 1

Preparation and Evaluation of an Embodied Coolant Device

A sealed packet was made of low density polypropylene (LDPE), which contained 5 and 10 ml of water as follows: the packet was sealed by soldering on three sides and one side was left open (FIG. 1A). 2.5 and 5 ml of water, respectively was introduced into the bags and the bags were oriented to create a center fold 1-10 (FIG. 1B), with spot welding 1-20 conducted at the site of the fold (FIG. 1C). The bags were then sealed with soldering, as well. This packet is referred to herein as the water packet. The dimensions of the components were as follows: the size of the internal water bag was 70×50 mm, the size of external urea-containing bag was 110×60 mm, and the thickness of the final assembled package was approximately 1-10 mm, depending upon the region of cross section.

A second packet was prepared, into which the water packet 2-10 inserts (FIG. 2). The second packet was comprised of a bi-layer material 2-20. The internal layer contained a non-woven absorbent material (non woven fabric), in this case, the inner layer was made from the super absorbent polymer non woven polypropylene and the outer later was made of a soft, water resistant material polypropylene film.

The bi-layer material was then soldered on three sides, much as the water packet was prepared, and the water packet was placed within the multi-layered packet. 5 grams of powdered urea was then placed inside the multi-layered packet, and the remaining opening of the multi-layered packet was then soldered, creating an enclosed packet.

Care was taken to ensure that the soldering/sealing of the multi-layered packet resulted in a seaming of the ends of both the water packet and multi-layered packet together, with the resulting complex forming an embodied coolant device comprising a part of this invention. In some embodiments, assembly of the multi-layered components is by lamination of the layers.

One of the two lateral edges of the coolant device was then gripped securely and slight pressure was applied to pull the edges outward, laterally. Referring for example, to FIG. 5B, the coolant device 5-30 was pulled from the package. The pulling on the edges of the device resulted in the rupture of the spot welding of the water packet, causing water to leak into the multi-layered packet. Within as little as 20 seconds, the endothermic reaction progressed sufficiently to achieve as much as a 20 degree temperature drop.

It will be apparent that if the pulling of the device from the package is not sufficient to activate the mechanism, then an end of each device may be grasped in each hand, respectively, and pulled laterally, to activate the cooling mechanism.

Table 1 plots the various conditions employed in assembling the described coolant devices, and resulting temperature cooling effects obtained with the same. A thermocouple measures temperature changes in the material Table 1:

| Water/Urea | Time | Temp [Fahrenheit] | Temp [Celsius] |
| --- | --- | --- | --- |
| 5 ml/5 g | 0 | 80 | 26.8 |
| | 00:20 | 45 | 7.3 |
| | 01:25 | 47 | 8.4 |
| | 02:00 | 49 | 9.5 |
| | 02:30 | 53 | 11.7 |
| | 03:30 | 55 | 12.7 |
| | 04:40 | 55 | 13 |
| | 06:00 | 58 | 14.5 |
| | 07:00 | 60 | 15.8 |
| | 09:00 | 62 | 16.4 |
| | 10:00 | 64 | 17.8 |
| | 11:00 | 64 | 17.7 |
| | 13:00 | 66 | 18.9 |
| | 14:00 | 66 | 19 |
| | 15:00 | 70 | 21 |
| 10 ml/5 g | 00:00 | 80 | 26.6 |
| | 00:50 | 61 | 16 |
| | 01:00 | 61 | 16.2 |
| | 02:00 | 62 | 16.5 |
| | 03:00 | 64 | 17.5 |
| | 04:00 | 64 | 18 |
| | 05:00 | 65 | 18.3 |
| | 06:00 | 66 | 19 |
| | 07:00 | 68 | 20 |
| | 09:00 | 69 | 20.7 |
| | 10:00 | 70 | 21 |
| | 11:00 | 71 | 21.5 |
| | 12:00 | 71 | 21.8 |
| | 13:00 | 72 | 22.5 |
| | 15:00 | 73 | 23 |
| 15 ml/5 g | 00:00 | 80 | 26.6 |
| | 00:10 | 66 | 18.9 |
| | 00:25 | 67 | 19.6 |
| | 0.055555556 | 68 | 20 |
| | 0.097222222 | 67 | 19.6 |

As can be seen in Table 1, in each case, the temperature was lowered as compared to baseline, with the most significant reduction occurring when the ratio of the amount of urea in grams and volume of water used in ml is 1 to 1. In some embodiments, the invention contemplates further increasing the relative amount of urea to water, which will produce even greater temperature reduction.

Placement of the various embodied coolant devices to the surface of a skin of volunteers was carried out and the subjects reported a noticeable cooling effect on the skin when the device was applied.

Thus a coolant device was prepared, which device created an endothermic reaction, resulting in a cooling effect, when the device was placed on the surface of a skin of a subject.

Example 2

Design of Additional Embodied Coolant Devices

Example 1 provides a working example of embodied coolant devices. It is of course possible to further engineer the devices.

In some embodiments, one side or both sides of the coolant device may be further adapted to contain an absorbant material on its exterior, which absorbant material may absorb sweat from the subject to which the device is applied. The purpose of such a material is to provide quick and discreet comfort to the subject, while making use of the coolant activity of the device due to the endothermic reaction occurring in the device interior. The device does not particularly rely upon a wicking effect in order to achieve the cooling effect of the application of the device.

It is also envisioned that in the preparation of the multi-layered packet containing the water packet and urea located therewithin that the urea is combined in the manufacturing process with a pulp, based on the same principle as the combination of pulp and super absorbent polymers (SAP) are combined in order to create absorbant diapers or sanitary napkins.

In other embodiments, the urea may be placed between two layers of a non-woven material welded to form a closed packet, so that the powder does not move around too much within the packet.

In other embodiments, the inner packet is filled with a powder material containing powdered urea and powdered SAP.

Example 3

Design of Packaging for Embodied Coolant Devices

Examples 1-2 provide examples of embodied coolant devices. One of the benefits and aims of the subject invention is the creation of a highly discreet cooling device for use by women experiencing hot flashes.

It is envisioned that the design of the described device allows for very discreet cooling of the skin of the subject alleviating the discomfort of hot flashes, with a material, that for all intents and purposes appears to be a tissue.

In keeping with the desire for a discreet method of cooling using the device, it is also envisioned that a packaging material for the coolant tissues is constructed, which facilitates the activation of the endothermic reaction as part of the removal of the tissue from the packaging material.

Referring now to FIG. 3 and representing one embodiment of the invention, the coolant device is assembled such that the water pack 3-20 is located within the laminated packet, which is comprised of an inner absorbent layer 3-40 and an outer exposed water resistant layer 3-50. Urea 3-30 is located within the inner void created within the laminated packet. The urea may be combined with a pulp, as described hereinabove. An outer absorbent area 3-60 may be present on one side of the coolant device, if desired. FIG. 3A shows a perspective view, whereby one may readily envision how the sealing of the lateral ends 3-70 and 3-80, and seaming of the same within a dispenser packet 3-90 (FIG. 3C), whereby the opposing side is not seamed, and is located at the point of opening of the packet, 3-100, allows for the user to withdraw the coolant tissue from the packet, and because of the light seaming with the dispenser packet, or in another embodiment, perforation proximal to the region of seaming, allows for the breakage of the spot welding while extracting the coolant tissue from the packet.

It should also be clear to the skilled artisan that the coolant tissue can be removed from the packet and the cooling mechanism is then activated, with activation occurring manually, without any involvement of the dispenser packet in the activation mechanism.

Referring now to FIG. 4, the figure depicts embodied assemblies and organization of the first packet of the invention, including putative welding lines and creation of a fold in the packet, which comprises part of the activation mechanism of the coolant device. Fold line 4-10 in this embodiment is placed essentially at the midline, however the skilled artisan will appreciate that the fold line may be located at any convenient location. Putative welding lines 4-20, 4-30 and 4-40 are shown as well, however other welding lines may be envisioned, and the artisan will appreciate that the claimed invention is not limited in terms of placement of appropriate welding lines in the creation of the packets and devices of this invention.

Figure 4A:
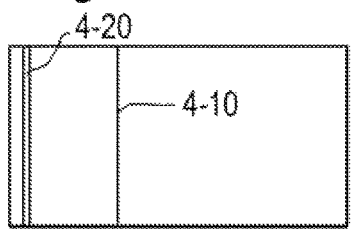
FIG. 4 schematically depicts an embodiment of a multiple unit dispenser containing an embodied cooling device of this invention.
Figure 4B:
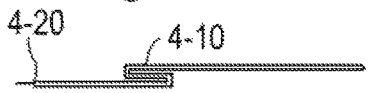
Figure 4C:
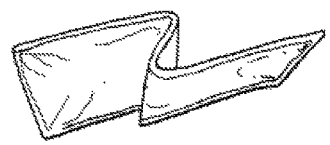
Figure 4D:
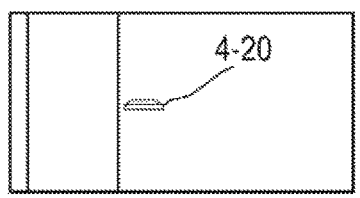
Figure 4E:
Figure 4F:
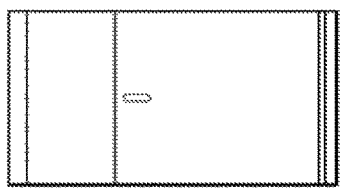
Figure 4G:
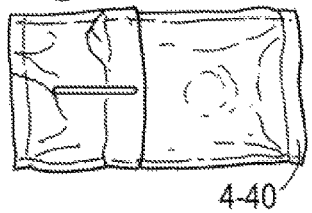
Figure 4H:
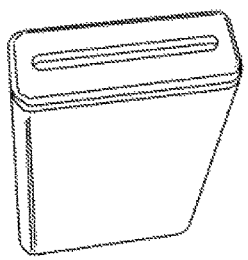
Figure 4I:
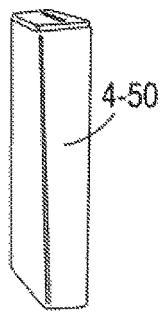
Figure 4J:
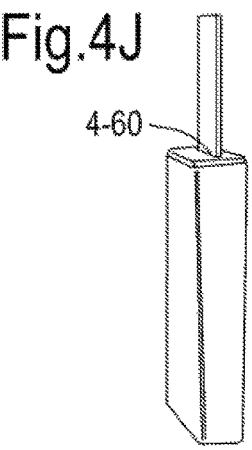
Figure 6A:
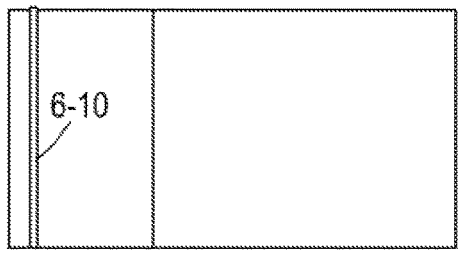
FIG. 6 schematically depicts another embodiment of the assembly and organization of an embodied cooling device of this invention, including potential welding lines for such assembly.
Figure 6B:
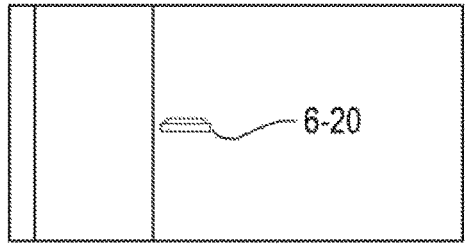
Figure 6C:
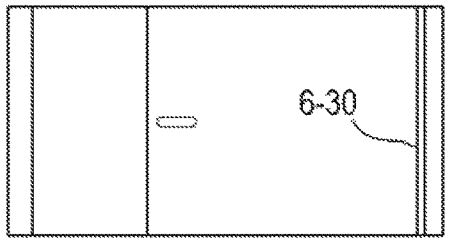
Figure 6D:
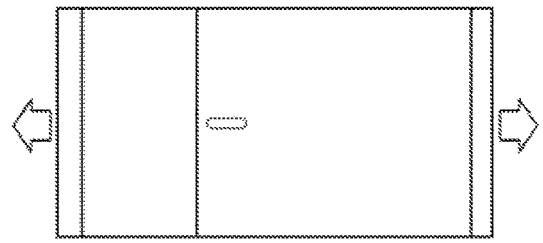

FIG. 4H-FIG. 4I provides another embodiment of a discreet package which facilitates the extraction of a coolant tissue from the packet while simultaneously activating the endothermic reaction within the coolant tissue is accomplished.

In this aspect, a number of coolant tissues 4-50 may be packaged in the dispenser pack. According to this embodiment, the slit opening 4-60, is threaded with an edge of the coolant tissue, so that the tissue may be readily extracted, however, the slit opening is of a dimension that results in rupture of the spot welding region, when the tissue is pulled through the slot opening, thereby activating the endothermic reaction.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In the claims articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A coolant device, comprising:
   a first packet, said first packet being comprised of a
      waterproof or water-resistant material and containing water sealed within said first packet, wherein said first packet comprises a fold, and said fold is further adapted to have a selectively permanent connection between external and internal layers of said fold, such that upon applying a force to laterally extend at least one end of said packet, a rupture of said first packet occurs allowing for the leakage of the water contained therewithin; a second packet which encases said first packet, said second packet comprising an exterior and interior layer, wherein said interior layer is comprised of an absorbant material and said exterior layer is comprised of a waterproof or water-resistant material and wherein an amount of a compound whose solvation in water results in an endothermic reaction is located within an interior of said second packet;

whereby upon lateral extension of at least one side of the second packet, a rupture of said first packet occurs allowing for the leakage of the water contained therewithin and its exposure to said urea located within said second packet, which exposure results in an endothermic reaction resulting in an outer surface of said second packet becoming cooler to the touch than an outer surface temperature prior to said rupture;

whereby one or more of:
said compound whose solvation in water results in an endothermic reaction is one or more of:
present in powdered form;
present in a ratio of the number of grams of said compound to the number of milliliters of water ranging from 3:1 to 0.5:1; and,
urea, ammonium nitrate, ammonium chloride or potassium chloride;
said interior layer of said second packet is comprised of a non woven polypropylene or polyethylene material;
said exterior surface of said second packet is further modified to incorporate a region containing a soft, thin, absorbant material; and,
wherein:
said first packet has dimensions of approximately between 30-90 mm on a side;
said second packet has dimensions of approximately between 35-220 mm wide and between 80-220 mm long; and
said device has a thickness of between 0.5-10 mm.

2. A single unit dispenser container containing a coolant device according to one or both of:
A) a first packet, said first packet being comprised of a waterproof or water-resistant material and containing water sealed within said first packet, wherein said first packet comprises a fold, and said fold is further adapted to have a selectively permanent connection between external and internal layers of said fold, such that upon applying a force to laterally extend at least one end of said packet, a rupture of said first packet occurs allowing for the leakage of the water contained therewithin; a second packet which encases said first packet, said second packet comprising an exterior and interior layer, wherein said interior layer is comprised of an absorbant material and said exterior layer is comprised of a waterproof or water-resistant material and wherein an amount of a compound whose solvation in water results in an endothermic reaction is located within an interior of said second packet; whereby upon lateral extension of at least one side of the second packet, a rupture of said first packet occurs allowing for the leakage of the water contained therewithin and its exposure to said urea located within said second packet, which exposure results in an endothermic reaction resulting in an outer surface of said second packet becoming cooler to the touch than an outer surface temperature prior to said rupture; and,
B) a first packet, said first packet being comprised of a waterproof material and containing an amount of a compound whose solvation in water results in an endothermic reaction; a second sealed packet comprising an inner layer comprised of a waterproof material which encases said first packet, said second packet comprising water and said first packet sealed therewithin, wherein selective rupture of said first packet within said second packet promotes leakage of said compound from said first packet and mixture of said compound with said water; whereby said leakage results in the occurrence of an endothermic reaction within said second sealed packet resulting in an outer surface of said second packet becoming cooler to the touch than an outer surface temperature prior to said rupture;
wherein at least one lateral surface of said second packet is fixedly adhered to an internal surface of said dispenser, such that, in order to extricate said second packet from said dispenser, at least a moderate force must be applied thereto, such moderate force being sufficient to cause a rupture in said first packet, releasing water located within said first packet into an interior of said second packet.

3. A multiple unit dispenser container comprising a coolant device according to one or both of:
A) a first packet, said first packet being comprised of a waterproof or water-resistant material and containing water sealed within said first packet, wherein said first packet comprises a fold, and said fold is further adapted to have a selectively permanent connection between external and internal layers of said fold, such that upon applying a force to laterally extend at least one end of said packet, a rupture of said first packet occurs allowing for the leakage of the water contained therewithin; a second packet which encases said first packet, said second packet comprising an exterior and interior layer, wherein said interior layer is comprised of an absorbant material and said exterior layer is comprised of a waterproof or water-resistant material and wherein an amount of a compound whose solvation in water results in an endothermic reaction is located within an interior of said second packet; whereby upon lateral extension of at least one side of the second packet, a rupture of said first packet occurs allowing for the leakage of the water contained therewithin and its exposure to said urea located within said second packet, which exposure results in an endothermic reaction resulting in an outer surface of said second packet becoming cooler to the touch than an outer surface temperature prior to said rupture; and,
B) a first packet, said first packet being comprised of a waterproof material and containing an amount of a compound whose solvation in water results in an endothermic reaction; a second sealed packet comprising an inner layer comprised of a waterproof material which encases said first packet, said second packet comprising water and said first packet sealed therewithin, wherein selective rupture of said first packet within said second packet promotes leakage of said compound from said first packet and mixture of said compound with said water; whereby said leakage results in the occurrence of an endothermic reaction within said second sealed packet resulting in an outer surface of said second packet becoming cooler to the touch than an outer surface temperature prior to said rupture;

wherein said dispenser container is in the form of a box of packet, comprising at least one top surface which is substantially rigid, and wherein said top surface comprises a slit like opening, which opening has a depth sufficient to accommodate minimal engagement of a lateral surface of said second packet therewithin; and said slit like opening is of a width that is narrower than a width at the region of said fold in said first packet, such that, upon extrication of said second packet from said dispenser, at least a moderate force must be applied thereto, such moderate force being sufficient to cause a rupture in said first packet, releasing water located within said first packet into an interior of said second packet.

4. A method for of combating discomfort associated with a rise in temperature at a skin surface, said method comprising:

laterally extending at least two sides of a second packet of a coolant device of one or both of:

A) a first packet, said first packet being comprised of a waterproof or water-resistant material and containing water sealed within said first packet, wherein said first packet comprises a fold, and said fold is further adapted to have a selectively permanent connection between external and internal layers of said fold, such that upon applying a force to laterally extend at least one end of said packet, a rupture of said first packet occurs allowing for the leakage of the water contained therewithin; a second packet which encases said first packet, said second packet comprising an exterior and interior layer, wherein said interior layer is comprised of an absorbant material and said exterior layer is comprised of a waterproof or water-resistant material and wherein an amount of a compound whose solvation in water results in an endothermic reaction is located within an interior of said second packet; whereby upon lateral extension of at least one side of the second packet, a rupture of said first packet occurs allowing for the leakage of the water contained therewithin and its exposure to said urea located within said second packet, which exposure results in an endothermic reaction resulting in an outer surface of said second packet becoming cooler to the touch than an outer surface temperature prior to said rupture; and, B) a first packet, said first packet being comprised of a waterproof material and containing an amount of a compound whose solvation in water results in an endothermic reaction; a second sealed packet comprising an inner layer comprised of a waterproof material which encases said first packet, said second packet comprising water and said first packet sealed therewithin, wherein selective rupture of said first packet within said second packet promotes leakage of said compound from said first packet and mixture of said compound with said water; whereby said leakage results in the occurrence of an endothermic reaction within said second sealed packet resulting in an outer surface of said second packet becoming cooler to the touch than an outer surface temperature prior to said rupture;

to cause a rupture of said first packet allowing for the leakage of the water contained therewithin and its exposure to said urea located within said second packet, which exposure results in an endothermic reaction resulting in an outer surface of said second packet becoming cooler to the touch than an outer surface temperature prior to said rupture resulting in an activated coolant device; and applying said activated coolant device to a skin surface for which the application of the same results in an alleviation of said discomfort on demand.

5. A coolant device, comprising:

a first packet, said first packet being comprised of a waterproof material and containing an amount of a compound whose solvation in water results in an endothermic reaction;

a second sealed packet comprising an inner layer comprised of a waterproof material which encases said first packet, said second packet comprising water and said first packet sealed therewithin, wherein selective rupture of said first packet within said second packet promotes leakage of said compound from said first packet and mixture of said compound with said water;

whereby said leakage results in the occurrence of an endothermic reaction within said second sealed packet resulting in an outer surface of said second packet becoming cooler to the touch than an outer surface temperature prior to said rupture;

whereby one or more of:

wherein said compound whose solvation in water results in an endothermic reaction is urea, ammonium nitrate, ammonium chloride or potassium chloride;

wherein said first packet comprises a dispersing agent which facilitates dispersion of said compound within said water following said rupture;

wherein said first packet is comprised of a material that is substantially hydrophobic;

wherein said device has a thickness of between 0.5-10 mm; and, wherein an exterior surface of said second packet is further modified to incorporate a region containing a thin, soft, absorbant material.

6. A coolant device, comprising:

a first packet, said first packet being comprised of a waterproof material and containing an amount of a compound whose solvation in water results in an endothermic reaction;

a second sealed packet comprising an inner layer comprised of a waterproof material which encases said first packet, said second packet comprising water and said first packet sealed therewithin, wherein selective rupture of said first packet within said second packet promotes leakage of said compound from said first packet and mixture of said compound with said water;

whereby said leakage results in the occurrence of an endothermic reaction within said second sealed packet resulting in an outer surface of said second packet becoming cooler to the touch than an outer surface temperature prior to said rupture;

wherein said compound whose solvation in water results in an endothermic reaction is present in a ratio of the number of grams of said compound to the number of milliliters of water ranging from 3:1 to 0.5:1.

* * * * *